(12) United States Patent
Olsen et al.

(10) Patent No.: US 9,999,634 B2
(45) Date of Patent: Jun. 19, 2018

(54) DISSOLUTION STABILITY OF CALCIUM CARBONATE TABLETS

(71) Applicant: Takeda AS, Asker (NO)

(72) Inventors: Peder Mohr Olsen, Kirke Hyllinge (DK); Poul Egon Bertelsen, Roskilde (DK); Thomas Thisted, Kibæk (DK); Henrik Ravn Aage, Copenhagen (DK)

(73) Assignee: Takeda AS, Asker (NO)

(*) Notice: Subject to any disclaimer, the term of this patent is extended or adjusted under 35 U.S.C. 154(b) by 0 days. days.

(21) Appl. No.: 14/808,420

(22) Filed: Jul. 24, 2015

(65) Prior Publication Data

US 2016/0022732 A1 Jan. 28, 2016

Related U.S. Application Data (63) Continuation of application No. 13/129,664, filed as application No. PCT/EP2009/008157 on Nov. 17, 2009, now Pat. No. 9,101,565.

(30) Foreign Application Priority Data

Nov. 17, 2008 (EP) .................. 08169264

(51) Int. Cl.
| | | |
|---|---|---|
| *A61K 33/10* | (2006.01) | |
| *A61K 9/20* | (2006.01) | |
| *A61K 33/06* | (2006.01) | |
| *A61J 3/10* | (2006.01) | |
| *A61K 9/28* | (2006.01) | |

(52) U.S. Cl.
CPC ............ *A61K 33/10* (2013.01); *A61J 3/10* (2013.01); *A61K 9/2018* (2013.01); *A61K 9/2072* (2013.01); *A61K 9/2095* (2013.01); *A61K 9/282* (2013.01); *A61K 33/06* (2013.01)

(58) Field of Classification Search
None
See application file for complete search history.

(56) References Cited

U.S. PATENT DOCUMENTS

| 4,115,553 | A | 9/1978 | Rubino et al. |
|---|---|---|---|
| 5,846,506 | A | 12/1998 | Esch et al. |
| 6,149,941 | A | 11/2000 | Schwarz et al. |
| 6,716,454 | B2 | 4/2004 | Meignant et al. |
| 9,101,565 | B2 | 8/2015 | Olsen et al. |
| 2002/0193355 | A1 | 12/2002 | Meignant et al. |
| 2004/0071772 | A1 | 4/2004 | Narita et al. |

FOREIGN PATENT DOCUMENTS

| DE | 20216314 U1 | 1/2004 |
|---|---|---|
| EP | 0647591 A1 | 4/1995 |
| EP | 0872240 A1 | 10/1998 |
| EP | 0914818 A1 | 5/1999 |
| EP | 1369131 A1 | 12/2003 |
| JP | 2001/316249 A | 11/2001 |
| JP | 5306229 B2 | 10/2013 |
| WO | WO-1992/10168 A1 | 6/1992 |
| WO | WO-1995/08273 A1 | 3/1995 |
| WO | WO-1996/09036 A1 | 3/1996 |
| WO | WO-1997/41835 A1 | 11/1997 |
| WO | WO-1999/06051 A1 | 2/1999 |
| WO | WO-2000/28973 A1 | 5/2000 |
| WO | WO-2003/055500 A1 | 7/2003 |
| WO | WO-2005/115342 A1 | 12/2005 |
| WO | WO-2005/117829 A2 | 12/2005 |

OTHER PUBLICATIONS

European Pharmacopoeia 7.0, 2.9.3 Dissolution test for solid dosage forms, p. 20903 (2010).
European Pharmacopoeia 7.0, 2.9.7 Uniformity of Content of Single-Dose Preparations, p. 20906 (2008).
European Pharmacopoeia 7.0, 2.9.8 Resistance to Crushing of Tablets, p. 20908 (2008).
European Pharmacopoeia 7.1, 2.9.1 Disintegration of tablets and capsules, p. 20901 (2011).
International Preliminary Report for Patentability for PCT/EP2009/008157, dated Nov. 16, 2010.
International Search Report for PCT/EP2009/008157, dated Oct. 3, 2010.
Jahn et al., Drug Development and Industrial Pharmacy, 31: 951-957 (2005).
Klobes, P. et al., Porosity and specific surface area measurements for solid materials, NIST National Institute of Standards and Technology (2006).
Notice of Opposition dated Aug. 16, 2011 in Opposition to European Patent No. 1755578.
Written Opinion for PCT/EP2009/008157, dated Oct. 3, 2010.

*Primary Examiner* — Tigabu Kassa
(74) *Attorney, Agent, or Firm* — Choate, Hall & Stewart LLP; Charles E. Lyon (57) ABSTRACT

The present invention relates to a method for the preparation of a tablet comprising at least 50% w/w of calcium carbonate, the method comprising
  i) providing a particulate composition comprising a) calcium carbonate, b) a binding sugar alcohol selected from sorbitol or isomalt, or combinations thereof, c) a non-binding sugar alcohol selected from mannitol, maltitol or xylitol, or combinations thereof, and
  ii) compressing said composition using a tabletting machine equipped with at least one pair of punches and dies, wherein the pair of punches and die before filling the die with said particulate composition is sprayed with a composition comprising a lubricant selected from magnesium stearate, calcium stearate or stearic acid or combinations thereof.

14 Claims, 6 Drawing Sheets

DISSOLUTION STABILITY OF CALCIUM CARBONATE TABLETS

This application is a continuation of U.S. patent application Ser. No. 13/129,664, which is filed on Aug. 1, 2011, which is a 371 application of PCT/EP2009/008157 which is filed on Nov. 17, 2009, which is now U.S. Pat. No. 9,101,565.

FIELD OF THE INVENTION

The present invention relates to a method for the preparation of calcium carbonate tablets, which method results in tablets that have improved storage stability with respect to dissolution characteristics. The method involves the use of a sugar alcohol with binding properties, notably sorbitol and/or isomalt, the use of a sugar alcohol without binding properties, notably selected from mannitol, maltitol or xylitol, and external application of a lubricant to the punches and dies of the tablet machine. In the event that the concentration of sorbitol does not exceed 10% w/w, the lubricant may also be admixed to a mixture containing i) calcium carbonate, ii) the sugar alcohol with binding properties, and iii) the sugar alcohol without binding properties. If, in the latter case, a stearate salt of an alkaline earth metal is employed, the concentration should be relatively low, e.g. not exceeding 0.35% w/w (based on the final powder mix to be compressed into tablets)

Thus, the invention provides also an alternative method for the preparation of calcium carbonate tablets with the above-mentioned advantage with respect to dissolution stability. This alternative method involves the use of internally applied lubricant, but requires use of a sugar alcohol with binding properties and another sugar alcohol without significant binding properties. Moreover, the concentration of the sugar alcohol with binding properties must not exceed 10% of the total composition.

The present invention also relates to the tablets obtained by the methods of the invention.

BACKGROUND OF THE INVENTION

Calcium is essential for a number of key functions in the body, both as ionized calcium and a calcium complex (Campell A K. Clin Sci 1987; 72:1-10). Cell behaviour and growth are regulated by calcium. In association with troponin, calcium controls muscle contraction and relaxation (Ebashi S. Proc R Soc Lond 1980; 207:259-86).

Calcium selected channels are a universal feature of the cell membrane and the electrical activity of nerve tissue and the discharge of neurosecretory granules are a function of the balance between intracellular and extra cellular calcium levels (Burgoyne R D. Biochim Biophys Acta 1984; 779: 201-16). The secretion of hormones and the activity of key enzymes and proteins are dependent on calcium. Finally calcium as a calcium phosphate complex confers rigidity and strength on the skeleton (Boskey A L. Springer, 1988: 171-26). Because bone contains over 99% of the total body calcium, skeletal calcium also serves as the major long-term calcium reservoir.

Calcium salts such as, e.g., calcium carbonate is used as a source of calcium especially for patients suffering from or at risk of osteoporosis. Moreover, calcium carbonate is used as an acid-neutralizing agent in antacid tablets.

Calcium salts like e.g. calcium carbonate is used in tablets and due to the high dose of calcium required, such tablets are often in the form of chewable tablets. It is a challenge to formulate chewable tablets containing a calcium salt, which tablets have a pleasant taste and an acceptable mouthfeel without the characteristic dominating taste or feeling of chalk.

Furthermore, i) the high dose of calcium carbonate (normally 300-600 mg of elemental calcium twice daily, corresponding to 750-1500 mg of calcium carbonate twice daily), ii) in general the inherent poor properties of calcium carbonate with respect to tabletting properties like compactability, calls for the need of adding one or more pharmaceutically acceptable excipients in order to obtain a suitable compactability, and iii) the extremely bad taste or mouthfeel of a calcium salt itself especially with respect to chalkiness make it very difficult to prepare a tablet that has a suitable small size, which is conveniently small for a patient to ingest either by swallowing or chewing. Sufficient taste masking is another major challenge when formulating chewable tablets.

As described in WO 2005/117829, the Applicant has found an easy way for producing tablets containing a physiologically tolerable calcium-containing compound by using a granulate comprising agglomerates of the calcium-containing compound. The granulate is obtained without use of any solvent (e.g. water), but involves the technique of roller compaction of the calcium-containing compound to form agglomerates having suitable properties for further processing into a solid dosage form such as, e.g., tablets.

Calcium carbonate tablets are well-described in the patent literature see e.g. WO 2005/117829, WO 2005/115342, WO 00/028973. From WO 2005/117829 are also known calcium carbonate tablets containing sorbitol and calcium carbonate tablet containing sorbitol and maltitol.

However, it has recently been found that when making calcium carbonate tablets for swallowing, the dissolution profile obtained during or immediate after production of the tablets may change over time. In other words the tablets are not stable with respect to dissolution. As long as the change is within acceptable limit (normally ±10%) the tablets are acceptable. However, the present inventors have observed situations, where there is a dramatic decrease in the dissolution profile, i.e. the release of calcium is i) much slower and/or ii) less complete. The present invention addresses this problem and provides a solution thereto.

DETAILED DISCLOSURE OF THE INVENTION

Accordingly, the present invention provides a method for the preparation of a calcium carbonate containing tablet that has a desired stability with respect to dissolution. Moreover, the present invention relates to novel calcium carbonate tablets that are stable with respect to dissolution behaviour.

If the dissolution profile changes during time, this is normally seen during the first 14 days after manufacture.

In the present context, a change in dissolution profile is determined by plotting the dissolution profile at time $t_0$ for the specific time points 10 min, 20 min 30 min and 60 min. In order for this profile to be acceptable the total amount of released calcium carbonate after 20, 30 and 60 min must be above 80%. This type of dissolution profile is plotted after approximately 14 days based on a repeated dissolution testing at that point in time. If the values at 20, 30 and 60 min are above 80% the tablets tested are stable with respect to dissolution profile provided that the tested tablets have been stored in open petri dishes at 25° C. and 60% relative humidity. Normally, the test is carried out immediately after production of the tablets or at least within the first week after production of the tablets.

The dissolution profile is obtained in accordance with pharmacopoeia requirements. Thus, the release of calcium is tested by dissolution testing using Ph. Eur. apparatus 2 (paddle), rotation 70 rpm, 1000 ml HCl 0.1 N and 37° measured on 3 tablets. The testing is carried out initially and after 14 days of storage in open petri dishes at 25° C. and 60% Relative Humidity (RH). This test is generally applicable in order to test whether the composition is stable with respect to dissolution profile.

In accordance with the above, the present invention provides a method for the preparation of a tablet comprising at least 50% w/w of calcium carbonate, the method comprising i) providing a particulate composition comprising a) calcium carbonate, b) a binding sugar alcohol selected from sorbitol or isomalt, or combinations thereof, c) a non-binding sugar alcohol selected from mannitol, maltitol or xylitol, or combinations thereof, and ii) compressing said composition using a tabletting machine equipped with at least one pair of punches and dies, wherein the pair of punches and die before filling the die with said particulate composition is sprayed with a lubricant selected from magnesium stearate, calcium stearate or stearic acid or combinations thereof.

In the present context, the terms "sugar alcohol with binding properties" or "binding sugar alcohol" denote a sugar alcohol that when compressed into a tablet as described in Example 1 herein using a compaction force of 5 kN has a crushing strength of 20 N or more and/or when compressed into a tablet as described in Example 1 herein using a compaction force of 10 kN has a crushing strength of 60 N or more. Sorbitol and isomalt are examples of such sugar alcohols.

When roller compaction is used to prepare the tablets of the present invention, the sugar alcohol with binding properties employed normally has a mean particle size of at the most about 150 μm such as, e.g., at the most about 110 μm, at the most about 100 μm, at the most about 90 μm, at the most about 80 μm, at the most about 70 μm, at the most about 60 μm, at the most about 50 μm, at the most about 40 μm, at the most about 30 μm, at the most about 20 μm or about 10 μm. Thus, the particle size may have a mean particle size in a range of from about 5 to about 150 μm such as, e.g., from about 5 to about 110 μm or from about 5 to about 80 μm.

Notably, a suitable sorbitol used in the examples herein has a mean particle size in a range of from about 25 to about 50 μm such as, e.g., from about 35 to about 45 μm or from about 30 to about 45 μm. Another suitable sorbitol used in the examples herein has a mean particle size in a range from about 50 to about 150 μm such as, e.g. from about 75 to about 125 μm or from about 100 to about 120 μm or 110 μm.

A suitable quality of isomalt with respect to particle size is isomalt that has a mean particle size in a range of from about 20 to about 50 μm such as, e.g., from about 25 to about 35 μm or from about 20 to about 35 μm. Another suitable quality of isomalt has a mean particle size in a range from about 50 to about 150 μm such as, e.g. from about 75 to about 125 μm or from about 100 to about 120 μm or 110 μm.

Moreover, in the present context, the terms "sugar alcohol without binding properties", "sugar alcohol without significant binding properties", or "non-binding sugar alcohol" denote a sugar alcohol that when compressed into a tablet as described above using a compaction force of 5 kN has a crushing strength of 20 N or less and/or when compressed into a tablet as described above using a compaction force of 10 kN has a crushing strength of 60 N or less. Mannitol, maltitol and xylitol are examples of such sugar alcohols.

It is contemplated that other sugar alcohols either having binding properties or being without such properties also can be used in accordance with the present invention. Such sugar alcohols are typically selected from the group consisting of mannitol, xylitol, maltitol, inositol, and lactitol, and mixtures thereof. Examples are Sorbitols, Neosorb P100T, Sorbidex P1666B0 and Sorbogem Fines Crystalline Sorbitol available from Roquette Freres, Cerestar and SPI Polyols Inc. respectively. Maltisorb P90 (maltitol) available from Roquette Freres, Xylitol CM50, Fructofin CM (fructose) and Lactitol CM50 available from Danisco Sweeteners, Isomalt ST-PF, Isomalt DC100, Gaio Tagatose and Manitol available from Palatinit, Arla Foods and Roquette, Freres respectively. Further examples of suitable saccharide-based binders/sweeteners include sucrose, dextrose.

A suitable tabletting machine that can be used in order to test the binding properties of sugar alcohols is equipped with data acquisition that as a minimum measures the compaction force applied.

As seen from Example 1 herein the crushing strength can suitably be measured by use of a Schleuniger-2E from the company Dr. Schleuniger and determined as the mean of measuring the crushing strength for 10 individual tablets.

For the preparation of tablets it is generally necessary to add one or more pharmaceutically acceptable excipients (e.g. lubricants) in order to avoid adherence and/or increase flowability of the granulate obtained. Accordingly, the method may also comprise a step of mixing the granulate obtained with one or more pharmaceutically acceptable excipients. As discussed below, the present inventors have observed that in order to achieve a suitable dissolution stability, there are situations where the lubricant advantageously can be added externally, i.e. sprayed directly on the punches and dies of the tabletting machine, namely when the calcium carbonate tablets contain a binding sugar alcohol like sorbitol and/or isomalt (note: the lubricant may be added internally provided that sorbitol is employed in a relatively low concentration).

External application of a lubricant such as magnesium stearate, calcium stearate or stearic acid, is an important feature of an aspect of the present invention. As seen from the examples herein, the dissolution profiles obtained vary over time (during the first 14 days after manufacture) in the event that the lubricant is added to the granulate before compression. However, if the lubricant is sprayed on the dies and punches by use of pressurized air before tabletting, then the present inventors have found that the desired stability with respect to dissolution are obtained.

A method of the present invention typically involves the use of roller compaction to agglomerate the calcium carbonate notably in the presence of one or more sugar alcohols. The Applicant has previously found that roller compaction of calcium carbonate together with e.g. sorbitol leads to an agglomerate that easily can be manufactured into tablets. However, it is contemplated that other related methods than roller compaction also can lead to a suitable result such as, e.g., slugging.

Thus, in a method according to the present invention the particulate composition in step i) above is prepared by the steps of:

i) roller compacting calcium carbonate and a binding sugar alcohol selected from sorbitol or isomalt, or combinations thereof and a non-binding sugar alcohol a non-binding sugar alcohol selected from mannitol, maltitol or xylitol, or combinations thereof to obtain a roller compacted granulate, and ii) if relevant, admixing one or more of said pharmaceutically acceptable excipients in a mixer.

Dependent on the concentration of sorbitol in the final powder mixture, a lubricant may be added to the particulate composition obtained by roller compaction or a related process (e.g. if the sorbitol concentration does not exceed 10% w/w), or externally to the tabletting equipment (independent on the sorbitol concentration).

The roller compaction process enables the powder material to establish binding forces between the individual particles, i.e. an increase in mean particle size is observed Establishment of a granulate (or agglomerate) is important when tablets are prepared in order to ensure a proper flowability and a fixation in the granulate (or agglomerate) of the components that make up the tablet. If this is not the case, there is a major risk for de-mixing of the components during manufacture, which normally results in unsatisfactory properties with respect to the pharmacopoeia requirement with respect to mass variation and dose variation.

As previously described, the process of roller compacting of a powder is applied as an alternative method to known granulation or agglomeration methods, i.e. wet granulation or—when tablets are prepared—direct compression using dry binders. The present inventors have found that the process of roller compacting does not destroy the possibility of obtaining products that have an acceptable mouth feel and at the same time are without a dominating chalk-like taste or feel. Normally, roller compaction is employed with the purpose of increasing the bulk density of a particular substance or composition e.g. in order to transform a bulky material to a less voluminous material that is easier to use in the manufacturing of pharmaceutical compositions which is not the main purpose where the objective primarily is to agglomerate the material.

Calcium carbonate is dosed in relatively high amount and, accordingly, it is important that the drug load is relatively high in order to avoid a tablet size that is too large. This is generally of most interest if the tablet is intended for swallowing, but even in the case of a chewing tablet, a patient prefer a tablet that is not too large in size. Accordingly, the excipients that are used in order to enable manufacturing of tablets should normally be kept at a relatively low concentration.

The total concentration of sugar alcohols present in the tablet composition is from about 15% to about 35% w/w such as from about 20% to about 25% w/w. Such concentrations make it possible to manufacture calcium carbonate tablets that have a concentration of calcium carbonate of at least 50% w/w. As seen from the examples herein a much higher drug load is possible such as at least 60% w/w, at least 65% w/w or at least 70% w/w.

Apart from the binding sugar alcohol, the examples herein show that incorporation of a non-binding sugar alcohol together with the binding sugar alcohol leads to the desired dissolution stability. The total concentration of the non-binding sugar alcohol(s) in a tablet of the invention is at least 1% w/w such as at least 2% w/w, at least 3% w/w or at least 4% w/w. As seen from the examples herein, suitable combinations of binding sugar alcohols and non-binding sugar alcohols are typically:

| Binding sugar alcohol (% w/w of total tablet composition) | Non-binding sugar alcohol (% w/w of total tablet composition) |
|---|---|
| 3-5 | 15-20 |
| 5-10 | 10-20 |
| 10-15 | 5-20 |
| 15-20 | 1-10 |
| 20-25 | 1-5 |

By use of the above-mentioned method using externally employed lubricant, tablets having the following composition are obtained:

It is important to emphasize that if the content of sorbitol in the calcium tablet does not exceed 10% w/w, then a lubricant like e.g., an alkaline earth stearate salt may be employed in a total concentration of from about 0.26% w/w-0.44% w/w, such as from about 0.3% w/w-0.4% w/w. In a preferred embodiment an alkaline earth stearate salt is employed in a concentration of about 0.35% w/w. The very low concentrations mentioned below correspond to the amount of lubricant applied during compression by spraying the compression tools with a dispersion/solution containing the lubricant. However, a person skilled in the art will based on the present disclosure understand that if the sorbitol concentration is low, then it is also—or alternatively— possible to admix the lubricant to the particulate material before compression, although the concentration should be in a concentration that is lower than normally used, i.e. lower than 5% w/w. In the present examples it is shown that a concentration of up to 0.35% w/w gives suitable results.

A calcium carbonate tablet containing:
70-75% w/w of calcium carbonate,
4-25% w/w of one or more binding sugar alcohols,
4-25% w/w of one or more non-binding sugar alcohols,
2-10% w/w of one or more pharmaceutically acceptable excipients (e.g. binders, fillers, additives etc.—not lubricants like magnesium stearate, calcium stearate or stearic acid)
0-2% w/w of one or more flavours, artificial sweeteners or the like,
0.001-0.01% w/w of magnesium stearate, calcium stearate or stearic acid,
with the proviso that the total amount corresponds to 100% w/w.

A calcium carbonate tablet containing:
70-75% w/w of calcium carbonate,
4-25% w/w of sorbitol,
4-25% w/w of one or more of mannitol, maltitol or xylitol,
2-10% w/w of one or more pharmaceutically acceptable excipients (e.g. binders, fillers, additives etc.—not lubricants like magnesium stearate, calcium stearate or stearic acid),
0-2% w/w of one or more flavours, artificial sweeteners or the like,
0.001-0.01% w/w of magnesium stearate, calcium stearate or stearic acid with the proviso that the total amount corresponds to 100% w/w.

A calcium carbonate tablet containing
70-75% w/w of calcium carbonate,
4-25% w/w of isomalt,
4-25% w/w of one or more of mannitol, maltitol or xylitol,
2-10% w/w of one or more pharmaceutically acceptable excipients (e.g. binders, fillers, additives etc.—not lubricants like magnesium stearate, calcium stearate or stearic acid),
0-2% w/w of one or more flavours, artificial sweeteners or the like, and
0.001-0.01% w/w of magnesium stearate, calcium stearate or stearic acid
with the proviso that the total amount corresponds to 100% w/w.

A calcium carbonate tablet containing:
70-75% w/w of calcium carbonate,
10-25% w/w of one or more binding sugar alcohols,
4-15% w/w of one or more non-binding sugar alcohols,
2-10% w/w of one or more pharmaceutically acceptable excipients (e.g. binders, fillers, additives etc.—not lubricants like magnesium stearate, calcium stearate or stearic acid,)
0-2% w/w of one or more flavours, artificial sweeteners or the like,
0.001-0.01% w/w of magnesium stearate, calcium stearate or stearic acid
with the proviso that the total amount corresponds to 100% w/w.

Moreover, the present inventors have observed that a suitable stability with respect to dissolution also can be obtained by a method for the preparation of a tablet comprising at least 70% w/w of calcium carbonate, the method comprising i) roller compacting a) calcium carbonate, b) a binding sugar alcohol selected from sorbitol or isomalt, or combinations thereof, and c) a non-binding sugar alcohol selected from mannitol, maltitol or xylitol, or combinations thereof to obtain a roller compacted granulate,
ii) admixing a lubricant and, optionally, one or more of said pharmaceutically acceptable excipients in a mixer, and
iii) compressing said composition using a tabletting machine, provided that the concentration of sorbitol in the tablet composition does not exceed 10% w/w.

Thus, in this case, the lubricant has been added internally to the granulate before compression. The details with respect to dissolution stability, concentration of isomalt, if present, concentration of non-binding sugars etc. are the same as described above, when the lubricant is externally applied. The only differences are with respect to the maximum content of sorbitol and the concentration of lubricant present in the tablets that in this case is somewhat higher than in the tablets prepared by externally applying the lubricant. As seen from the examples herein a suitable lubricant is magnesium stearate used in a concentration of 0.35% w/w (based on the total weight of the tablet). Use of magnesium stearate in a concentration of 0.45% w/w lead to tablets with a unsatisfactory dissolution profile (calcium was released too slow) and when magnesium stearate was used in a concentration of 0.25% w/w, adhesion to punches and dies was observed.

A suitable tablet prepared by internal application of a lubricant is:
a calcium carbonate tablet containing:
70-75% w/w of calcium carbonate,
2-10% w/w of one or more binding sugar alcohols,
4-25% w/w of one or more non-binding sugar alcohols,
2-10% w/w of one or more pharmaceutically acceptable excipients (e.g. binders, fillers, additives etc.—not lubricants like magnesium stearate, calcium stearate or stearic acid)
0-2% w/w of one or more flavours, artificial sweeteners or the like,
0.26-0.44% w/w of magnesium stearate, calcium stearate or stearic acid
with the proviso that the total amount corresponds to 100% w/w.

a calcium carbonate tablet containing:
70-75% w/w of calcium carbonate,
2-10% w/w of one or more binding sugar alcohols,
4-25% w/w of one or more non-binding sugar alcohols,
2-10% w/w of one or more pharmaceutically acceptable excipients (e.g. binders, fillers, additives etc.—not lubricants like magnesium stearate, calcium stearate or stearic acid)
0-2% w/w of one or more flavours, artificial sweeteners or the like,
0.3-0.4% w/w of magnesium stearate, calcium stearate or stearic acid
with the proviso that the total amount corresponds to 100% w/w.

a calcium carbonate tablet containing:
70-75% w/w of calcium carbonate,
2-10% w/w of one or more binding sugar alcohols,
4-25% w/w of one or more non-binding sugar alcohols,
2-10% w/w of one or more pharmaceutically acceptable excipients (e.g. binders, fillers, additives etc.—not lubricants like magnesium stearate, calcium stearate or stearic acid)
0-2% w/w of one or more flavours, artificial sweeteners or the like,
0.35% w/w of magnesium stearate, calcium stearate or stearic acid
with the proviso that the total amount corresponds to 100% w/w.

Calcium Carbonate

As mentioned previously, calcium has a number of important functions within the mammalian body in particular in humans.

Calcium salts like e.g. calcium carbonate is used in tablets and due to the high dose of calcium required, such tablets are often in the form of chewable tablets. It is a challenge to formulate e.g. chewable tablets containing a calcium salt, which tablets have a pleasant taste and an acceptable mouth feel without the characteristic dominating taste or feeling of chalk.

In the present invention calcium carbonate is employed as the active substance. It may be used in combination with other calcium salts provided that the tablets obtained have the desired properties with respect to dissolution stability.

Suitable other calcium salts for use in combination with calcium carbonate may be bisglycino calcium, calcium acetate, calcium carbonate, calcium chloride, calcium citrate, calcium citrate malate, calcium cornate, calcium fluoride, calcium glubionate, calcium gluconate, calcium glycerophosphate, calcium hydrogen phosphate, calcium hydroxyapatite, calcium lactate, calcium lactobionate, calcium lactogluconate, calcium phosphate, calcium pidolate, calcium stearate and tricalcium phosphate.

Normally, a tablet made according to the invention contains an amount of the calcium-containing compound corresponding to from about 100 to about 1000 mg Ca such as, e.g., from about 150 to about 800 mg, from about 200 to about 700 mg, from about 200 to about 600 mg or from about 200 to about 500 mg Ca.

Calcium carbonate can be in three different crystal structures: calcite, aragonite and vaterite. Mineralogically, these are specific mineral phases, which relate to the distinct arrangement of the calcium, carbon and oxygen atoms in the crystal structure. These distinct phases influence the shape and symmetry of the crystal forms. For example, calcite is available in four different shapes: scalenohedral, prismatic, spherical and rhombohedral, and aragonit crystals can be obtained as e.g. discrete or clustered needle-like shapes. Other shapes are also available such as, e.g., cubic shapes (Scoralite from Scora).

As shown in the examples herein, a particular suitable quality of calcium carbonate is calcium carbonate having a mean particle size of 60 μm or less such as, e.g., 50 μm or less or 40 μm or less.

Furthermore, an interesting quality of calcium carbonate has a bulk density below 2 g/mL.

Calcium carbonate 2064 Merck (available from Merck, Darmstadt, Germany) that has a mean particle size of 10-30 μm, an apparent bulk density of 0.4 to 0.7 g/mL, and a specific surface area of 0.3 $m^2/g$;

Calcium carbonate 2069 Merck (available from Merck, Darmstadt, Germany) that has a mean particle size of approx. 3.9 μm, and an apparent bulk density of 0.4 to 0.7 g/mL;

Scoralite 1A (available from Scora Watrigant S A, France) has a mean particle size of 5 to 20 μm, an apparent bulk density of 0.7 to 1.0 g/mL, and a specific surface area of 0.6 $m^2/g$;

Scoralite 1B (available from Scora Watrigant S A, France) has a mean particle size of 10-25 μm, an apparent bulk density of 0.9 to 1.2 g/mL, and a specific surface area of 0.4 to 0.6 $m^2/g$;

Scoralite 1A+B (available from Scora Watrigant S A, France) have a mean particle size of 7-25 μm, an apparent bulk density of 0.7 to 1.2 g/mL, and a specific surface area of 0.35 to 0.8 $m^2/g$;

Pharmacarb LL (available from Chr. Hansen, Mahawah New Jersie) L has a mean particle size of 12-16 μm, an apparent bulk density of 1.0 to 1.5 g/mL, and a specific surface area of 0.7 $m^2/g$;

Sturcal H has a mean particle size of approx. 4 μm, an apparent bulk density of 0.48 to 0.61 g/mL;

Sturcal F has a mean particle size of approx. 2.5 μm, an apparent bulk density of 0.32 to 0.43 g/mL;

Sturcal M has a mean particle size of 7 μm, an apparent bulk density of 0.7 to 1.0 g/mL, and a specific surface area of 1.0 $m^2/g$;

Mikhart 10, SPL, 15, 40 and 65 (available from Provencale, Provencale, France);

Mikhart 10 has a mean particle size of 10 μm,

Mikhart SPL has a mean particle size of 20 μm,

Mikhart 15 has a mean particle size of 17 μm,

Mikhart 40 has a mean particle size of 30 μm, an apparent bulk density of 1.1 to 1.5 g/mL;

Mikhart 65 has a mean particle size of 60 μm, an apparent bulk density of 1.25 to 1.7 g/mL;

Omyapure 35, (available from Omya S.A.S, Paris, France) has a mean particle size of 5-30 μm, and a specific surface area of 2.9 $m^2/g$;

Socal P2PHV (available from Solvay, Brussels, Belgium) has a mean particle size of 1.5 μm, an apparent bulk density of 0.28 g/mL, and a specific surface area of 7.0 $m^2/g$;

Calci Pure 250 Heavy, Calci Pure 250 Extra Heavy and Calci Pure GCC HD 212 with a mean particle size of 10-30 μm, an apparent bulk density of 0.9-1.2 g/ml, and a specific surface area of 0.7 $m^2/g$ (available from Particle Dynamic Inc., St. Louis Mont.).

The content of the calcium-containing compound in a tablet made according to the present invention is in a range from about 50% to about 90% w/w such as, e.g., from about 55% to about 90% w/w, from about 60% to about 85% w/w, from about 65% to about 80% w/w or from about 70% to about 75% w/w.

Normally, the dose of calcium for therapeutic or prophylactic purposes is from about 350 mg (e.g. newborn) to about 1200 mg (lactating women) daily. The amount of the calcium-containing compound in the tablets can be adjusted so that the tablets are suitable for administration 1-4 times daily, preferably once or twice daily.

A person skilled in the art will know how to adjust the composition and the various process parameters in order to obtain a desired calcium-containing product.

In the event that it is desired to include other active substances than the calcium-containing compound, the method may also comprise a step of adding one or more therapeutically, prophylactically and/or diagnostically active substance to the granulate obtained.

Such substances include one or more nutrients such as, e.g., one or more vitamins or minerals. In a specific embodiment, the further active substance is a D-vitamin such as, e.g., $D_3$ vitamin, $D_2$ vitamin or derivatives thereof.

D Vitamin or Other Active Substances

A particulate material as well as a tablet obtained according to the invention may comprise a further therapeutically and/or prophylactically active substance. Of particular interest are one or more D-vitamin compounds. Non-limiting examples are dry vitamin D3, 100 CWS available from DSM and dry vitamin D3 100 GFP available from BASF.

A particulate material or tablet made according to the invention may comprise a further therapeutically and/or prophylactically active substance, or it may contain one or more nutrients such as, e.g. one or more vitamins or minerals. Of specific interest are e.g. vitamin B, vitamin C, vitamin D and/or vitamin K and minerals like e.g. zink, magnesium, selenium etc.

Of particular interest are one or more D-vitamin compounds such as, e.g., Vitamin $D_2$ (ergocalciferol) and Vitamin $D_3$ (cholecalciferol) including dry vitamin $D_3$, 100 CWS available from DSM and dry vitamin $D_3$ 100 GFP available from BASF.

In addition to its action on calcium and skeletal homeostasis, vitamin D is involved in the regulation of several major systems in the body. The actions of vitamin D are medicated at the genome by a complex formed by 1,25-$(OH)_2$ vitamin D mainly produced in the kidney, with the vitamin D receptor (VDR). The latter is widely distributed in many cell types. The 1,25-$(OH)_2$ vitamin D/VDR complex has important regulatory roles in cell differentiation and in the immune system. Some of these actions are probably dependant on the ability of certain tissues other than the kidney to produce 1,25-$(OH)_2$ vitamin D locally and act as a paracrine (Adams J S et al. Endocrinology 1996; 137: 4514-7).

In humans, deficiency of vitamin D results in rickets in children and osteomalacia in adults. The basic abnormality is a delay in the rate of mineralization off osteoid as it is laid down by the osteoblast (Peacock M. London Livingstone, 1993:83-118). It is not clear whether this delay is due to a failure of a 1,25-(OH)$_2$ vitamin D—dependant mechanism in the osteoblast or to reduced supplies of calcium and phosphate secondary to malabsorption or a combination of both. Accompanying the mineralization delay, there is reduced supply of calcium and phosphate, severe secondary hyperparathyroidism with hypocalcaemia and hypophosphatemia and increased bone turnover.

Vitamin D insufficiency, the preclinical phase of vitamin D deficiency, also causes a reduced calcium supply and secondary hyperparathyroidism, albeit of a milder degree than found with deficiency. If this state remains chronic, osteopenia results. The biochemical process underlying this state of calcium insufficiency is probably inappropriate level of 1,25-(OH)$_2$ vitamin D due to a reduction in its substrate 25-OHD (Francis R M et al. Eur J Clin Invest 1983; 13:391-6). The state of vitamin D insufficiency is most commonly found in the elderly. With age there is a decrease in serum 25-OH vitamin D due to decreased sunlight exposure and possible to decreased skin synthesis. Furthermore, in the elderly the condition is exacerbated by a decrease in calcium intake and a paradoxical decrease in calcium absorption. The reduction in renal function with age giving rise to reduced renal 1,25-(OH)$_2$ vitamin D production may be a contributing factor. There are a number of studies of the effects of vitamin D supplementation on bone loss in the elderly. Some are without calcium supplementation and others are with calcium supplementation. It appears from the studies that although vitamin D supplementation is necessary to reverse deficiency and insufficiency, it is even more important as far as the skeleton is concerned to provide calcium supplementation since the major skeletal defect is calcium deficiency. In literature based on clinical trials, recent findings suggest trends of need for higher doses of vitamin D for the elderly patients (Compston J E. BMJ 1998; 317:1466-67). An open quasi-randomised study of annual injections of 150.000-300.000 IU of vitamin D (corresponding to approx. 400-800 IU/day) showed a significant reduction in overall fracture rate but not in the rate of hip fracture in treated patients (Heikinheimo R J et al. Calcif Tissue Int 1992; 51:105-110).

As it appears from above, a combination of calcium and vitamin D is of interest. The recommended Daily Allowance (RDA) of calcium and vitamin D$_3$ are as follows (European Commission. Report on osteoporosis in the European Community. Action for prevention. Office for official Publications of the European Communities, Luxembourg 1998):

| Group | Age (years) | Calcium (mg)* | Vitamin D$_3$ (µg) |
|---|---|---|---|
| Newborn | 0-0.5 | 400 | 10-25 |
|  | 0.5-1.0 | 360-400 | 10-25 |
| Children | 1.0-3.0 | 400-600 | 10 |
|  | 4.0-7.0 | 450-600 | 0-10 |
|  | 8.0-10 | 550-700 | 0-10 |
| Men | 11-17 | 900-1000 | 0-10 |
|  | 18-24 | 900-1000 | 0-15 |
|  | 25-65 | 700-800 | 0-10 |
|  | 65+ | 700-800 | 10 |
| Women | 11-17 | 900-1000 | 0-15 |
|  | 18-24 | 900-1000 | 0-10 |
|  | 25-50 | 700-800 | 0-10 |
|  | 51-65 | 800 | 0-10 |
|  | 65+ | 700-800 | 10 |
| Pregnant |  | 700-900 | 10 |
| Lactating |  | 1200 | 10 |

*RDA of calcium varies from country to country and is being re-evaluated in many countries.

Pharmaceutically Acceptable Excipients

In the present context, the term "pharmaceutically acceptable excipient" is intended to denote any material, which is inert in the sense that it substantially does not have any therapeutic and/or prophylactic effect per se. A pharmaceutically acceptable excipient may be added to the active drug substance with the purpose of making it possible to obtain a pharmaceutical composition, which has acceptable technical properties. Although a pharmaceutically acceptable excipient may have some influence on the release of the active drug substance, materials useful for obtaining modified release are not included in this definition.

The calcium-containing compound (in the present context: calcium carbonate) and the sugar alcohol may also be admixed with one or more pharmaceutically acceptable excipients before or after roller compaction. Such excipients include those normally used in formulation of solid dosage forms such as, e.g. fillers, binders, disintegrants, lubricants, flavouring agents, colouring agents, including sweeteners, pH adjusting agents, stabilizing agents, etc.

Typically, a disintegrant is selected from the group consisting of: croscarmellose sodium (a cross-linked polymer of carboxymethylcellulose sodium), crospovidone, starch NF; polacrilin sodium or potassium and sodium starch glycolate. Those skilled in the art will appreciate that it is desirable for compressible tablets to disintegrate within 30 minutes, more desirable within 10 min, most desirable within 5 min; therefore, the disintegrant used preferably results in the disintegration of the tablet within 30 minutes, more preferable within 10 min, most preferable within 5 min.

Examples of disintegrants that may be used are e.g. cellulose derivatives, including microcrystalline cellulose, low-substituted hydroxypropyl cellulose (e.g. LH 22, LH 21, LH 20, LH 32, LH 31, LH30); starches, including potato starch; croscarmellose sodium (i.e. cross-linked carboxymethylcellulose sodium salt; e.g. Ac-Di-Sol®); alginic acid or alginates; insoluble polyvinylpyrrolidone (e.g. Polyvidon® CL, Polyvidon® CL-M, Kollidon® CL, Polyplasdone® XL, Polyplasdone® XL-10); sodium carboxymethyl starch (e.g. Primogel® and Explotab®).

Fillers/diluents/binders may be incorporated such as polyols, sucrose, sorbitol, mannitol, Erythritol®, Tagatose®, lactose (e.g., spray-dried lactose, α-lactose, β-lactose, Tabletose®, various grades of Pharmatose®, Microtose or Fast-Floc®), microcrystalline cellulose (e.g., various grades of Avicel®, such as Avicel® PH101, Avicel® PH102 or Avicel® PH105, Elcema® P100, Emcocel®, Vivacel®, Ming Tai® and Solka-Floc®), hydroxypropylcellulose, L-hydroxypropylcellulose (low-substituted) (e.g. L-HPC-CH31, L-HPC-LH11, LH 22, LH 21, LH 20, LH 32, LH 31, LH30), dextrins, maltodextrins (e.g. Lodex® 5 and Lodex® 10), starches or modified starches (including potato starch, maize starch and rice starch), sodium chloride, sodium phosphate, calcium sulfate, calcium carbonate.

In pharmaceutical compositions made according to the present invention, especially microcrystalline cellulose, L-hydroxypropylcellulose, dextrins, maltodextrins, starches and modified starches have proved to be well suited.

In a specific embodiment of the invention, the calcium-containing compound may be roller compacted together with one or more pharmaceutically acceptable binders, or a binder may be added after roller compaction. Suitable binders include those normally used within the pharmaceutical field although binders usually employed in wet granulation processes are not likely to be able to function to the same extent as essentially no liquid is present in during the agglomeration.

More specifically, examples include
cellulose derivates including methylcellulose, hydroxypropylcellulose (HPC, L-HPC), hydroxypropylmethylcellulose (HPMC), microcrystalline cellulose (MCC), sodium carboxymethylcellulose (Na-CMC), etc.;
mono- di-, oligo-, polysaccharides including dextrose, fructose, glucose, isomalt, lactose, maltose, sucrose, tagatose, trehalose, inulin and maltodextrin;
polyols including sugar alcohols such as, e.g, lactitol, maltitol, mannitol, sorbitol, xylitol and inositol;
polyvinylpyrrolidone including Kollidon K30, Kollidon 90F or Kollidon VA64 and
proteins including casein.

Surfactants may be employed such as non-ionic (e.g., polysorbate 20, polysorbate 21, polysorbate 40, polysorbate 60, polysorbate 61, polysorbate 65, polysorbate 80, polysorbate 81, polysorbate 85, polysorbate 120, sorbitane monoisostearate, sorbitanmonolaurate, sorbitan monopalmitate, sorbitan monostearate, sorbitan monooleate, sorbitan sesquioleate, sorbitan trioleate, glyceryl monooleate and polyvinylalkohol), anionic (e.g., docusate sodium and sodium lauryl sulphate) and cationic (e.g., benzalkonium chloride, benzethonium chloride and cetrimide) or mixtures thereof.

Other appropriate pharmaceutically acceptable excipients may include colorants, flavouring agents, and buffering agents.

Tablets may comprise a sweetener selected from the group consisting of dextrose, fructose, glycerin, glucose, lactitol, lactose, maltose, sucrose, tagatose, trehalose, alitame, aspartame, acesulfam potassium, cyclamic acid, cyclamate salt (e.g. calcium cyclamate, sodium cyclamate), sucralose, neohesperidine dihydrochalcone, thaumatin, saccharin, saccharin salt (e.g. ammonium saccharin, calcium saccharin, potassium saccharin, sodium saccharin), and mixtures thereof.

The tablets obtained by a method of the invention may be provided with a coating provided that the coating does not substantially retard the release of the active drug substance from the composition. Typically, a film coating may be employed.

If desired known flavourants and known FD & C colorants can be added to the composition.

The invention is illustrated in the following examples without limiting the invention thereto.

EXAMPLES

Example 1 (Reference)

Test of Compactability of Different Sugar Alcohols

Tablets comprising either Neosorb P100T, Sorbidex P1666BO, Isomalt ST-PF, Maltisorb P90, Mannitol 60 or Xylitol CM50 were compressed on an instrumented Fette Exacta 1/F single punch tablet press, only maximum compression force on the upper punch was recorded.

Before the compression of each tablet the punch tips and the die bore were lubricated with a 5% suspension of magnesium stearate in acetone. The acetone was allowed to evaporate before compression of the tablet.

The sugar alcohol was weighed, transferred to the die bore and then compressed, see table 1. Immediately after ejection the tablet was tested for crushing strength.

TABLE 1

| Sugar alcohol | Trade name | Compact weight |
| --- | --- | --- |
| Sorbitol | Neosorb P100T | 530 mg |
|  | Sorbidex P1666BO | 400 mg |
| Isomalt | Isomalt ST-PF | 400 mg |
| Maltitol | Maltisorb P90 | 400 mg |
| Mannitol | Mannitol 60 | 400 mg |
| Xylitol | Xylitol CM50 | 400 mg |

It was assumed that the obtained tablet crushing strength of the sugar alcohols are independent of particle size and this was tested using sorbitol having two different mean particle sizes, 38 µm and 110 µm. From FIG. 1 (each point is the average of three measurements) it is seen that the assumption was correct. Therefore, test of particle size was not repeated for the other sugar alcohols.

Figure 1:
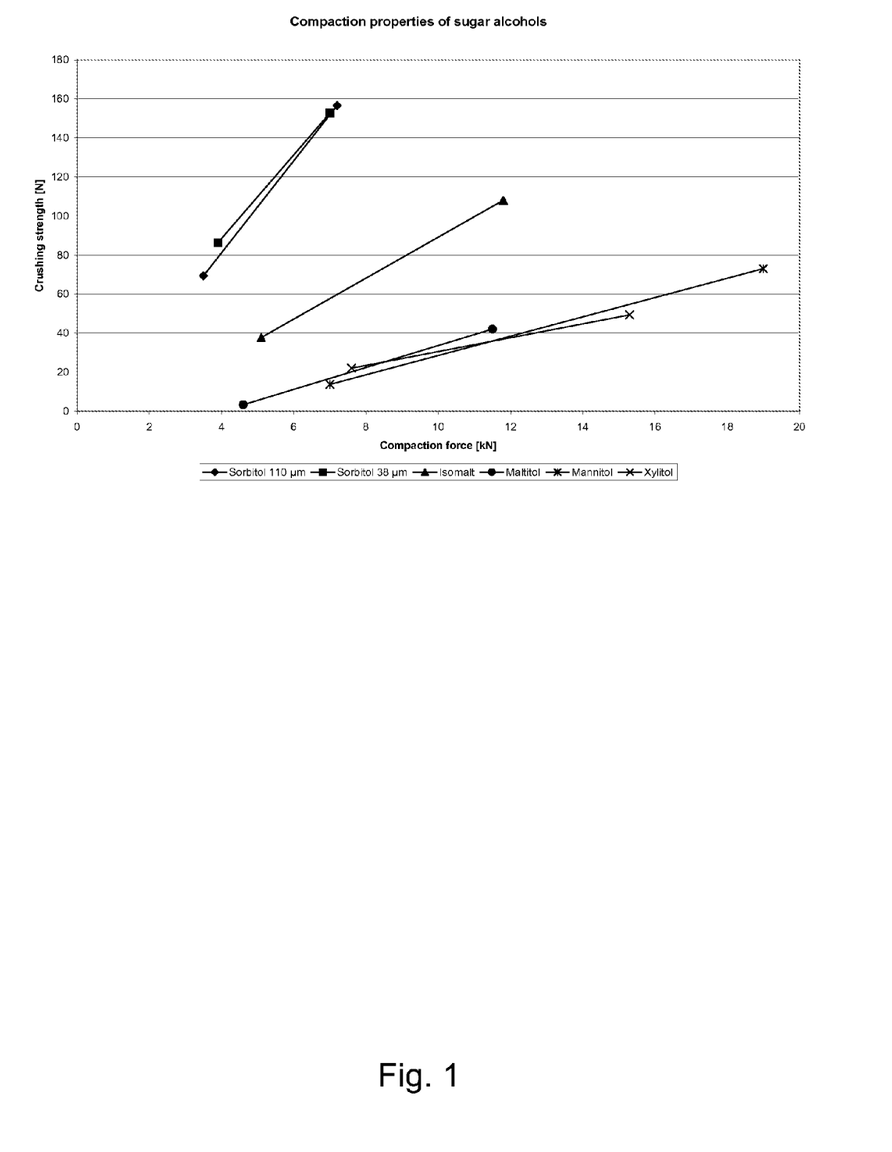
FIG. 1 depicts data related to compaction properties of sugar alcohols.

From FIG. 1 it can be seen that sorbitol have the best compactability resulting in the steepest slope of the correlation between compression force and crushing strength. Sorbitol is followed by isomalt. Maltitol, mannitol and xylitol have a very poor compactability.

The tabletting machine used is equipped with data acquisition that as a minimum measure the compaction force applied. However, any tabletting machine may be used provided the compaction force applied can be measured.

The crushing strength has been measured by use of a Schleuniger-2E from the company Dr. Schleuniger and determined as the mean of measuring the crushing strength for 10 individual tablets.

Example 2

Influence on Dissolution Stability of a Mixture of Binding and Non-Binding Sugar Alcohols Combined with Internal or External Lubrication In this example sorbitol has been chosen as the binding sugar alcohol and maltitol as the non-binding sugar alcohol.

TABLE 2

| | Composition of tablets [%] | | | | | | | |
| --- | --- | --- | --- | --- | --- | --- | --- | --- |
| Experiment | Calcium Carbonate | Sorbitol | Maltitol | MCC | Croscarmellose | Flavour | Sweetener | Mg-stearate |
| 23 | 72.59 | 8.94 | 13.41 | 3.25 | 1.16 | 0.58 | 0.06 | 0.00 |

Based on a batch size of approximately 20 kg tablets according to table 3 are manufactured in the following way:

Sorbitol and mannitol are delumped by use of a Quadro Comill. Thereafter, these are mixed with calcium carbonate by use of a tumble mixer. This mixture is roller compacted by use of a Gerteis 3W-Polygran roller compactor based on the following parameters: Gap size approx. 3.5 mm, compaction force (fixed) 12 kN/cm, roller speed 5 rpm, sieve size 1.5 mm. The remaining excipients are admixed to the hereby obtained granulate by use of a tumble mixer. This final mixture is compressed into tablets using a Fette 2090 rotary tablet press, capsule shape punch design (18.9 mm×9.4 mm) compression force aiming at a chrushing strength of 11 kP, tablet mass 1728 mg. Magnesium stearate has been added externally by use of a PKB2 magnesium stearate spraying system that sprays the magnesium stearate onto the tablet punches.

Release of calcium has been tested by dissolution testing using Ph. Eur. apparatus 2 (paddle), rotation 70 rpm, HCl 0.1 N and 37°, 3 tablets were tested. This has been carried out initially and after 14 days of storage in open petri dishes at 25° C. and 60% Relative Humitity (RH). This test is generally applicable in order to test whether the composition is stable with respect to dissolution profile.

Figure 2:
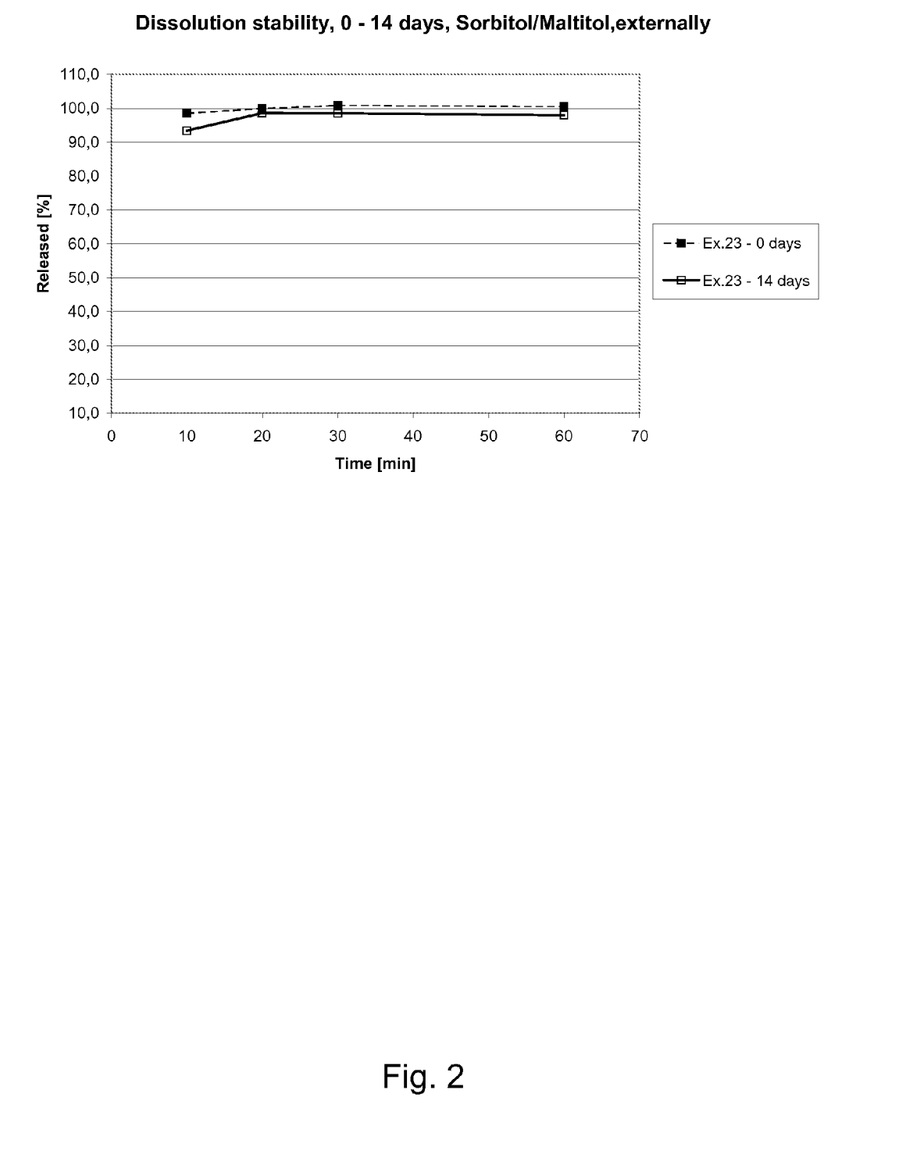
FIG. 2 depicts data related to dissolution stability over a period of 0-14 days for the formulation of Example 23, having the indicated combinations of sorbitol and maltitol, when magnesium stearate is added externally.

Results of dissolution testing are shown in FIG. 2

From this figure it can be seen that for external addition of magnesium stearate the dissolution is unaffected by storage for the tested relationships between sorbitol/maltitol.

Based on compositions in table 3 tablets are produced according to example 2.

However, for tablets in experiment 1-5 magnesium stearate has been added internally resulting in a tablet mass of 1728 mg, whereas for experiment 6-10 magnesium stearate has been added externally by use of a PKB2 magnesium stearate spraying system that sprays the magnesium stearate onto the tablet punches resulting in a tablet mass of 1722 mg.

In Experiment 1-5, the content of magnesium stearate was about 6 mg per tablet corresponding to about 0.35% w/w. In Experiments 6-10, about 30-50 µg magnesium stearate was deposited on the surface of the tablets during compressing.

Dissolution testing has been carried out according to example 2.

Figure 3:
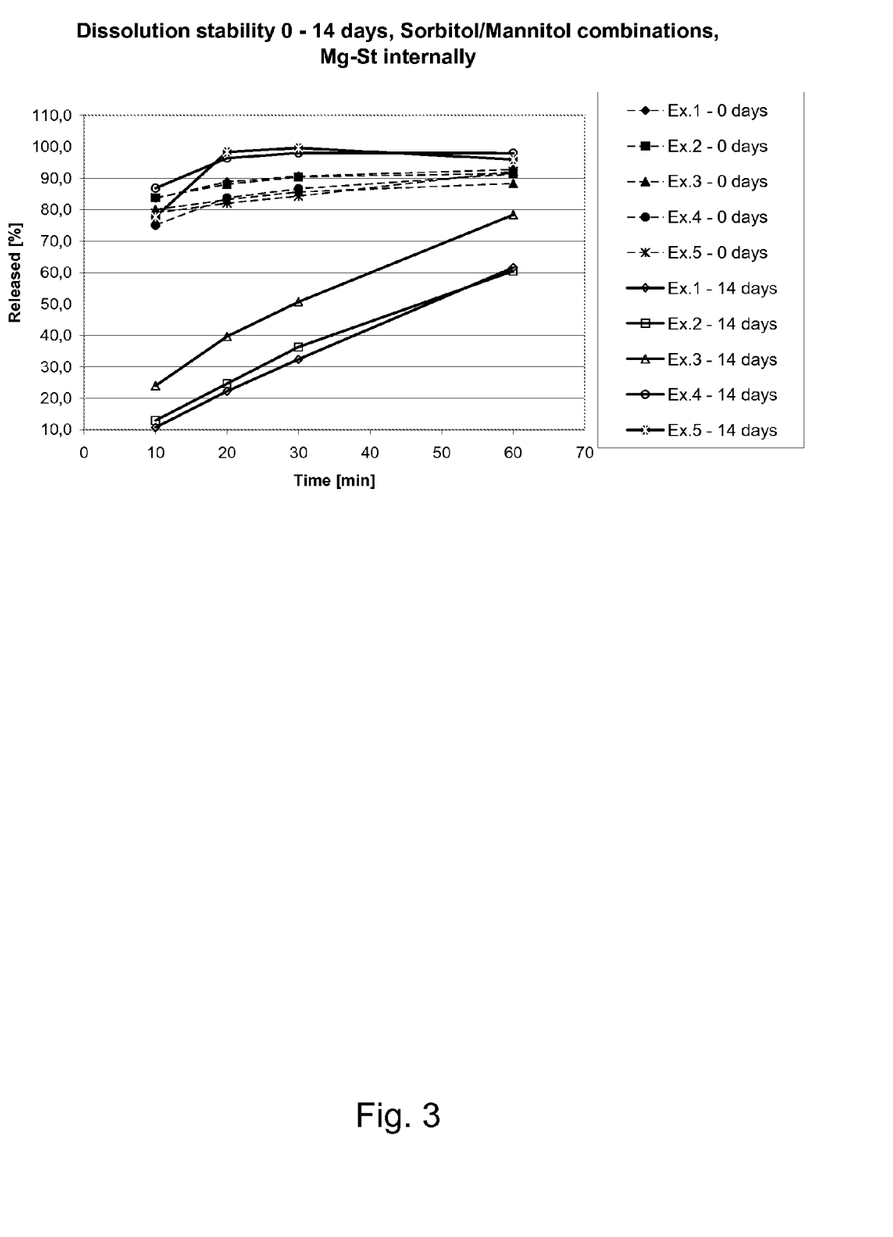
FIG. 3 depicts data related to dissolution stability over a period of 0-14 days for the formulations of Examples 1-5, having the indicated combinations of sorbitol and mannitol, when magnesium stearate is added internally.
Figure 4:
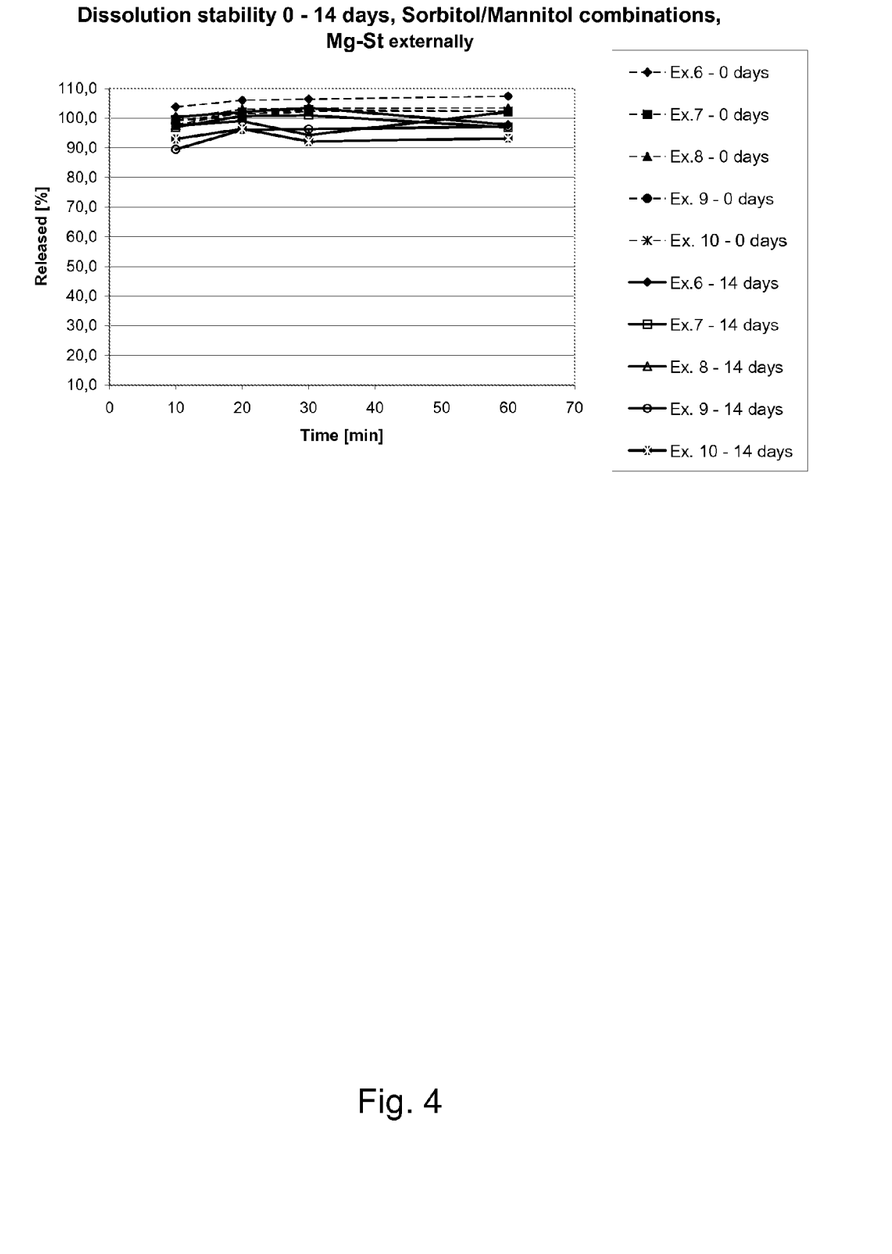
FIG. 4 depicts data related to dissolution stability over a period of 0-14 days for the formulations of Examples 6-10, having the indicated combinations of sorbitol and mannitol, when magnesium stearate is added externally.

The resulting dissolution profiles can be seen in the FIGS. 3 and 4.

From these figures it can be seen that when magnesium stearate is added internally (in tablet formulation) the dissolution profiles, FIG. 2, are initially unaffected by the amount of sorbitol in the formulation. However, already after 14 days the amount of sorbitol turns out to be critical resulting in unsatisfactory dissolution profiles for experiment 1-3. However, if magnesium stearate is added externally the amount of sorbitol has no impact on the stability of dissolution, FIG. 3.

Examples 2 and 3 illustrates that if magnesium stearate is added internally the dissolution profiles even being acceptable initially will when stored be affected by the relationship between the binding and non-binding sugar alcohols. If magnesium stearate is added externally this relationship has no impact on dissolution from tablets after storage.

Example 3

Influence on Dissolution Stability of a Mixture of Binding and Non-Binding Sugar Alcohols Combined with Internal or External Lubrication In this example sorbitol has been chosen as the binding sugar alcohol and mannitol as the non-binding sugar alcohol.

Example 4

Influence on Dissolution Stability of a Mixture of Two Binding Sugar Alcohols Combined with Internal or External Lubrication In this example sorbitol and isomalt have been chosen as binding sugar alcohols.

TABLE 3

Compositions of tablets [%]

| Experiment | Calcium Carbonate | Sorbitol | Mannitol | MCC | Croscarmellose | Flavour | Sweetener | Mg-stearate |
|---|---|---|---|---|---|---|---|---|
| 1 | 72.34 | 22.28 | 0 | 3.24 | 1.16 | 0.58 | 0.06 | 0.35 |
| 2 | 72.34 | 17.82 | 4.46 | 3.24 | 1.16 | 0.58 | 0.06 | 0.35 |
| 3 | 72.34 | 13.37 | 8.91 | 3.24 | 1.16 | 0.58 | 0.06 | 0.35 |
| 4 | 72.34 | 8.91 | 13.37 | 3.24 | 1.16 | 0.58 | 0.06 | 0.35 |
| 5 | 72.34 | 4.46 | 17.82 | 3.24 | 1.16 | 0.58 | 0.06 | 0.35 |
| 6 | 72.59 | 22.36 | 0.00 | 3.25 | 1.16 | 0.58 | 0.06 | 0 |
| 7 | 72.59 | 17.89 | 4.47 | 3.25 | 1.16 | 0.58 | 0.06 | 0 |
| 8 | 72.59 | 13.41 | 8.94 | 3.25 | 1.16 | 0.58 | 0.06 | 0 |
| 9 | 72.59 | 8.94 | 13.41 | 3.25 | 1.16 | 0.58 | 0.06 | 0 |
| 10 | 72.59 | 4.47 | 17.89 | 3.25 | 1.16 | 0.58 | 0.06 | 0 |

TABLE 4

Compositions of tablets [%]

| Experiment | Calcium Carbonate | Sorbitol | Isomalt | MCC | Croscarmellose | Flavour | Sweetener | Mg-stearate |
|---|---|---|---|---|---|---|---|---|
| 11 | 72.34 | 16.72 | 5.56 | 3.24 | 1.16 | 0.58 | 0.06 | 0.35 |
| 12 | 72.34 | 11.14 | 11.14 | 3.24 | 1.16 | 0.58 | 0.06 | 0.35 |
| 13 | 72.34 | 8.51 | 13.77 | 3.24 | 1.16 | 0.58 | 0.06 | 0.35 |
| 14 | 72.34 | 5.61 | 16.67 | 3.24 | 1.16 | 0.58 | 0.06 | 0.35 |
| 15 | 72.34 | 2.55 | 19.73 | 3.24 | 1.16 | 0.58 | 0.06 | 0.35 |
| 16 | 72.34 | 0 | 22.28 | 3.24 | 1.16 | 0.58 | 0.06 | 0.35 |
| 17 | 72.59 | 16.78 | 5.57 | 3.25 | 1.16 | 0.58 | 0.06 | 0 |
| 18 | 72.59 | 11.18 | 11.18 | 3.25 | 1.16 | 0.58 | 0.06 | 0 |
| 19 | 72.59 | 8.54 | 13.82 | 3.25 | 1.16 | 0.58 | 0.06 | 0 |
| 20 | 72.59 | 5.63 | 16.72 | 3.25 | 1.16 | 0.58 | 0.06 | 0 |
| 21 | 72.59 | 2.56 | 19.80 | 3.25 | 1.16 | 0.58 | 0.06 | 0 |
| 22 | 72.59 | 0 | 22.36 | 3.25 | 1.16 | 0.58 | 0.06 | 0 |

Based on composition in table 4 tablets are produced according to example 2.

However, tablets in experiment 11-16 magnesium stearate has been added internally resulting in a tablet mass of 1728 mg, whereas for experiment 17-22 magnesium stearate has been added externally by use of a PKB2 magnesium stearate spraying system that sprays the magnesium stearate onto the tablet punches resulting in a tablet mass of 1722 mg.

Dissolution testing has been carried out according to example 2. The resulting dissolution profiles can be seen in the FIGS. 5 and 6.

Figure 5:
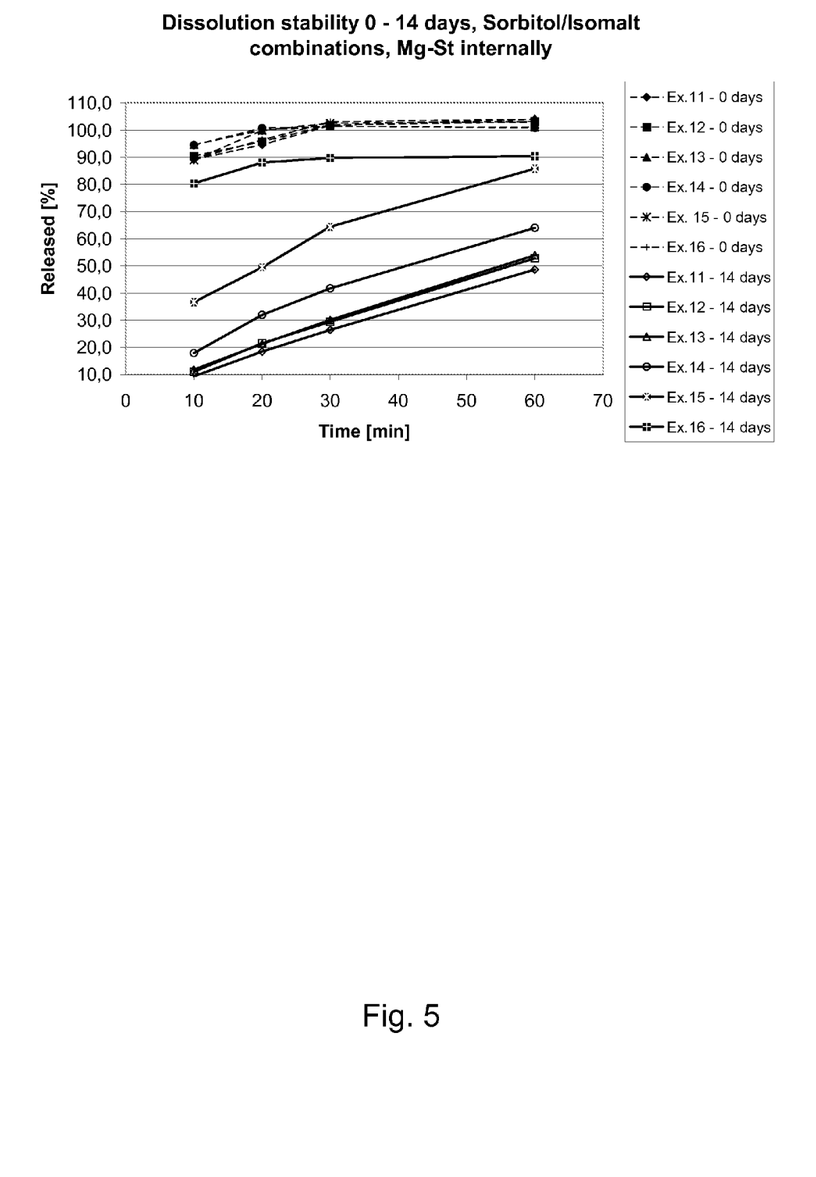
FIG. 5 depicts data related to dissolution stability over a period of 0-14 days for the formulations of Examples 11-16, having the indicated combinations of sorbitol and isomalt, when magnesium stearate is added internally.

From these figures it can be seen that when magnesium stearate is added internally (in the tablet formulation) the dissolution profiles, FIG. 5, are initially unaffected by the ratio between sorbitol and isomalt in the formulation. However, already after 14 days of storage at 25° C. and 60% RH in open petri dishes the amount of sorbitol turns out to be critical resulting in unsatisfactory dissolution profiles for all experiment. Furthermore, even if sorbitol is completely removed from the formulation, storage results in an suboptimal dissolution profile even though lowering the amount of sorbitol does reduce the impact.

Figure 6:
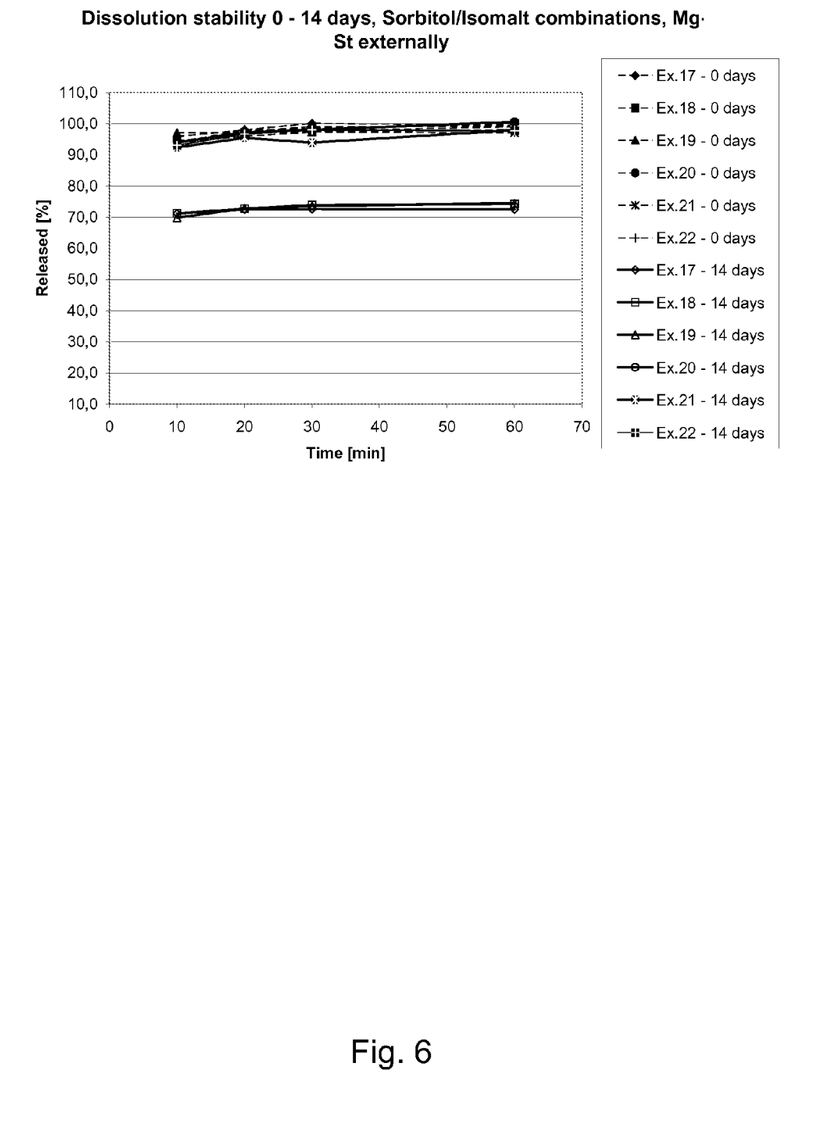
FIG. 6 depicts data related to dissolution stability over a period of 0-14 days for the formulations of Examples 17-22, having the indicated combinations of sorbitol and isomalt, when magnesium stearate is added externally.

In contrast to what is seen in example 3, for external addition of magnesium stearate, only a low amount of sorbitol leads to a dissolution profile unaffected by storage of tablets at 25° C. and 60 RH in open petri dishes, FIG. 6.

The invention claimed is:

1. A method for the preparation of a calcium carbonate tablet containing:
   70-75% w/w of calcium carbonate;
   5-15% w/w of one or more binding sugar alcohols selected from sorbitol, isomalt and combinations thereof;
   5-20% w/w of one or more non-binding sugar alcohols selected from mannitol, maltitol, xylitol and combinations thereof;
   2-10% w/w of one or more pharmaceutically acceptable excipients, wherein said excipients are not lubricants;
   0-2% w/w of one or more flavours or artificial sweeteners; and
   0.001-0.01% w/w of magnesium stearate, calcium stearate, stearic acid, or combinations thereof, wherein the magnesium stearate, calcium stearate, stearic acid or combinations thereof, is substantially present on the external surface of the tablet;
   with the proviso that the total amount of the calcium carbonate tablet corresponds to 100% w/w;
   the method comprising:
   i) roller compacting a) the calcium carbonate, b) the one or more binding sugar alcohols selected from sorbitol, isomalt and combinations thereof, c) the one or more non-binding sugar alcohols selected from mannitol, maltitol, xylitol and combinations thereof to obtain a roller compacted granulate;
   ii) admixing one or more of said pharmaceutically acceptable excipients and, optionally, one or more flavours or artificial sweeteners, in a mixer; and
   iii) compressing the resulting composition using a tabletting machine and applying on the external surface of the tablet the magnesium stearate, calcium stearate, stearic acid or combinations thereof.

2. A calcium carbonate tablet obtainable by a method as claimed in claim 1.

3. A calcium carbonate tablet containing:
   70-75% w/w of calcium carbonate;
   5-15% w/w of one or more binding sugar alcohols selected from sorbitol, isomalt and combinations thereof;
   5-20% w/w of one or more non-binding sugar alcohols selected from mannitol, maltitol, xylitol and combinations thereof;
   2-10% w/w of one or more pharmaceutically acceptable excipients, wherein said excipients are not lubricants;
   0-2% w/w of one or more flavours or artificial sweeteners; and
   0.001-0.01% w/w of magnesium stearate, calcium stearate, stearic acid or combinations thereof, wherein the magnesium stearate, calcium stearate, stearic acid or combinations thereof, is substantially present on the external surface of the tablet;
   with the proviso that the total amount of the calcium carbonate tablet corresponds to 100% w/w.

4. The calcium carbonate tablet of claim 3, containing 5-10% w/w of the one or more binding sugar alcohols.

5. The calcium carbonate tablet of claim 3, containing 10-15% w/w of the one or more binding sugar alcohols.

6. The calcium carbonate tablet of claim 3, containing 15-20% w/w of the one or more non-binding sugar alcohols.

7. The calcium carbonate tablet of claim 3, containing 5-10% w/w of the one or more binding sugar alcohols and 10-20% w/w of the one or more non-binding sugar alcohols.

8. The calcium carbonate tablet of claim 3, containing about 8.94% w/w of the one or more binding sugar alcohols.

9. The calcium carbonate tablet of claim 3, containing about 13.41% w/w of the one or more non-binding sugar alcohols.

10. The calcium carbonate tablet of claim 3, containing about 8.94% w/w of the one or more binding sugar alcohols and about 13.41% w/w of the one or more non-binding sugar alcohols.

11. The calcium carbonate tablet of claim 3, wherein the one or more binding sugar alcohols contains sorbitol.

12. The calcium carbonate tablet of claim 3, wherein the one or more non-binding sugar alcohols contains mannitol.

13. The calcium carbonate tablet of claim 3, the one or more binding sugar alcohols contains sorbitol and the one or more non-binding sugar alcohols contains mannitol.

14. The method of claim 1, wherein the magnesium stearate, calcium stearate, stearic acid or combinations thereof is applied to dies and/or punches of the tabletting machine and thereby applied to the external surface of the tablet upon compressing.

\* \* \* \* \*